(12) United States Patent
Yliruusi et al.

(10) Patent No.: US 6,531,463 B1
(45) Date of Patent: Mar. 11, 2003

(54) METHOD FOR PRODUCING A FAT MIXTURE

(75) Inventors: Jouko Yliruusi, Vantaa (FI); Raimo Hiltunen, Helsinki (FI); Leena Christiansen, Helsinki (FI)

(73) Assignee: Spice Sciences Oy, Helsinki (FI)

( * ) Notice: Subject to any disclaimer, the term of this patent is extended or adjusted under 35 U.S.C. 154(b) by 0 days.

(21) Appl. No.: 09/622,579

(22) PCT Filed: Feb. 15, 1999

(86) PCT No.: PCT/FI99/00121

§ 371 (c)(1),
(2), (4) Date: Nov. 13, 2000

(87) PCT Pub. No.: WO99/43218

PCT Pub. Date: Sep. 2, 1999

(30) Foreign Application Priority Data

Feb. 27, 1998 (FI) .................................................. 980450

(51) Int. Cl.⁷ ............................................... A61K 31/56
(52) U.S. Cl. ....................................... 514/182; 514/170
(58) Field of Search ................................... 514/170, 182

(56) References Cited

U.S. PATENT DOCUMENTS

| | | | | |
|---|---|---|---|---|
| 3,085,939 A | * | 4/1963 | Wruble et al. ................. | 167/65 |
| 3,751,569 A | | 8/1973 | Erickson ....................... | 424/173 |
| 3,865,939 A | | 2/1975 | James ......................... | 424/238 |
| 5,502,045 A | | 3/1996 | Miettinen et al. ............. | 514/182 |

FOREIGN PATENT DOCUMENTS

| | | |
|---|---|---|
| JP | 57206336 | 12/1982 |
| JP | 62148424 | 7/1987 |
| WO | 97/42830 | 11/1997 |

OTHER PUBLICATIONS

1975–18814W, Leningrad Food Res Inst: "Dietetic pastries contg. beta–sitosterol—for use by patients with lipid exchange disorder."
1979–66146B, Lith Food Ind Des: "Canned dietetic food mfr. —includes addn. of oil contg. beta–sitosterol before heating, useful in lipid metabolism disorders."
1983–10783K Ajinomoto KK, "Edible oil having cholesterol suppressing effect—contains vitamin–E and vegetable sterol."
1987–224314, Riken Vitamin CO, "Sterol–contg. composite for food industry, etc.—also contains specified emulsifier, and dispersant, e.g. liq. paraffin."

* cited by examiner

Primary Examiner—Barbara P. Badio
(74) Attorney, Agent, or Firm—Finnegan, Henderson, Farabow, Garrett & Dunner, L.L.P.

(57) ABSTRACT

A method for producing a fatty blend of β-sitosterol, or of β-sitosterol and β-sitostanol, which is useful for lowering the serum total cholesterol and LDL-cholesterol levels which method includes forming a mixture by dissolving 0.5–80 wt % of a starting material containing β-sitosterol, or β-sitosterol and β-sitostanol, in 5–90 wt % of oil or fat, or mixtures thereof, by heating at a temperature of 80–140° C. until the starting material containing β-sitosterol or β-sitosterol and β-sitostanol is dissolved; cooling the mixture to a temperature of 40–80° C.; during the cooling adding 5–30 wt % of water with a temperature essentially similar to that of the mixture to the mixture, and agitating the mixture and the water to form a homogeneous and stable dispersion of the mixture in the water, wherein the starting material containing β-sitosterol or β-sitosterol and β-sitostanol is partly dissolved and/or microcrystalline form. A composition made by the method can be mixed into ingredients of food products. Serum total cholesterol and LDL-cholesterol levels can be lowered by administration of the composition.

16 Claims, No Drawings

METHOD FOR PRODUCING A FAT MIXTURE

This application is a 371 of PCT/FI99/00121 filed Feb. 15, 1999.

FIELD OF THE INVENTION

The present invention relates to a method for producing a fat mixture of β-sitosterol, which mixture is health beneficial, homogeneous and stable, lowers the serum total cholesterol and LDL-cholesterol levels, and contains the β-sitosterol in a partly dissolved and/or microcrystalline form.

BACKGROUND OF THE INVENTION

A high serum total cholesterol level, hypertension and smoking are the main risk factors associated with a heart disease (1). There are several sterols of plant origin that are distinguished from cholesterol only by side chain substituents and by the degree of saturation. Most of the higher plants produce 24α-substituted sterols (24-methyl- and 24-ethylsterols). Sitosterols are mixtures of β-sitosterol (stigmasta-5-en-3β-ole) and certain saturated sterols, such as β-sitostanol, containing sterols not less than 95%, and unsaturated sterols not less than 85%. Sitosterols are broadly present in plants, such as in wheat and rye germ oils, corn oil, and commonly in seed oils. Sitosterols are antihypercholesterolemic agents that inhibit absorption of cholesterol in the intestine, and through the inner walls of blood vessels (2). Sitosterols play a role in the treatment of atherosclerosis when administered in doses of 2–3 grams., three times a day. In the western diet, the daily intake of β-sitosterol, stigmasterol and campesterol from food is about 200–400 mg (3), which is of about the same order as our daily cholesterol intake from food.

At the beginning of 1950's, it was recognized that as a result of the addition of β-sitosterol to the feed of cholesterol fed chicken and rabbits, the cholesterol levels were lowered in both test animals, and moreover, this addition of β-sitosterol prevented atherogenesis in rabbits (4). The use of sitosterol and soy bean sterols for lowering cholesterol levels was studied intensely in 1950's and 1960's (5), and indeed, preparations thereof lowered cholesterol levels by about 10% (6). It was then discovered that the activity of β-sitosterol was based on the inhibition of absorption of cholesterol, and that sterols of plant origin were themselves poorly absorbed (7). The mechanism which inhibits the cholesterol absorption was considered to be based on crystallization and coprecipitation of cholesterol and β-sitosterol. Mattson et al. (8) showed that 1 gram of β-sitosterol reduces by 42% the absorption of cholesterol from food containing 500 mg of cholesterol. The reduction of plasma cholesterol may be due to the increased activity of LDL-receptors.

β-Sitosterol is a lipophilic compound. In contact with the lipid membranes of intestinal walls, β-sitosterol will not be absorbed due to its poor water solubility, or only a minor proportion of it will be absorbed; when administered orally, only less than 5% of it will be absorbed (9). The activity of β-sitosterol is based on competitive inhibition of cholesterol absorption in the intestine (10). β-sitosterol interferes with cholesterol resorption and reresorption in the small intestine (11). It is considered that this results from the similarity between the chemical structures of cholesterol and β-sitosterol (12). Several studies carried out under various conditions have shown that phytosterols lower LDL-cholesterol levels. It is further recognized that serum phytosterols correlate with HDL-levels. β-sitosterol reduces synthesis of cholesterol in the liver by affecting the gene expression of HMG-CoA reductase (13). Richter W et al. (14) have shown that β-sitosterol lowers by 10–15% the total serum cholesterol level, and by 19% the LDL-cholesterol level, by inhibiting the absorption of cholesterol in the intestine. In a study, nine adult patients were administered for 5 days with 500 mg of cholesterol, as well as with 1 gram of β-sitosterol, or 2 grams of β-sitosteryl oleate. The absorption of cholesterol was decreased by 42% when administering β-sitosterol, and by 33% when administering β-sitoteryl oleate (15). Uchita et al. (16) have recognized that in female rats, sitosterol inhibits absorption of cholesterol, and lowers cholesterol balance in plasma and liver. Vahouny et al. (17) have discovered that sitosterol inhibits absorption of cholesterol in rats by 54%.

Finnish patent application No. 964951 discloses an agent for lowering the cholesterol level in serum, and the use thereof. This application relates to the use of an ester of β-sitostanol with a fatty acid or a mixture of esters of β-sitostanol with a fat acid as a fat component or as a fat substitute in food products, to the use thereof as such, complementing the diet, and to the compound itself.

Finnish patent publication No. 98 730 discloses a method for producing a substance to lower high serum cholesterol levels. In the method β-sitostanol, obtained from β-sitosterol by hydrogenating in an organic solvent in the presence of palladium on carbon as a catalyst, and a plant oil are used to produce an ester of β-sitostanol with a fatty acid, or a mixture of such esters, employing the transesterification technique in the presence of a sodium ethylate catalyst.

Both of these patent publications mentioned above disclose a method for modifying β-sitosterol to obtain a derivative thereof soluble in fats, wherein soluble β-sitostanol fatty acid esters are produced therefrom, as well as the use of the compounds obtained as agents to lower serum cholesterol levels.

Naturally occurring β-sitosterol is a crystalline compound. As is known, free sterols like β-sitosterol are dissolved only scarcely in oil and fat, and therefore, derivatives of β-sitosterol, for instance esters that are significantly more soluble in fats are produced for practical reasons, even though, according to some studies (15), these derivatives do not inhibit the absorption of cholesterol as effectively as the free β-sitosterol. Such derivatives soluble in fats may be mixed much more easily into nutrition products to form a homogeneous mixture than a solid, insoluble, coarse β-sitosterol powder. However, such processing to obtain a β-sitosterol derivative entails additional costs for the product. Further, the hydrogenation of β-sitosterol to β-sitostanol is necessarily carried out using an organic solvent so that traces of it, as well as traces of the metal catalysts used, may be present in the esterified end product. In addition, the esterified product is no longer a naturally occurring substance but a man made artificial chemical compound.

An object of the invention is to provide a method for producing a fat mixture of β-sitosterol, which is health beneficial, homogeneous and stable, lowers the total serum cholesterol and LDL-cholesterol levels, and contains the β-sitosterol in a partly dissolved and/or in a microcrystalline form. Another object of the invention is to use such a homogeneous stable fat mixture of β-sitosterol containing it in a partly dissolved and/or in a microcrystalline form in fat preparations or food products as an agent that lowers the cholesterol level in serum, as well as to use this mixture as such to complement the diet.

The main characteristic features of the method and use according to the present invention are disclosed in the appended claims.

We have discovered that β-sitosterol may be made partly soluble and/or micro-crystalline with the following procedure. The problems and disadvantages associated with the state of the art may be avoided with the solution of the present invention. According to the method of the invention, β-sitosterol and food grade oil are mixed, and this mixture is heated until all solids are dissolved in oil. After cooling, water is added into the mixture at the temperature thereof, thereby dispersing it. The result will be a homogeneous, stable, fat-like, almost white mass with a consistency closely resembling that of butter, or an oily mixture, depending on the amounts of the components. This homogeneous and stable paste is particularly suitable for being mixed into food products, for instance.

The starting material in this method is β-sitosterol that may comprise 80–100% of β-sitosterol and β-sitostanol, and as impurities 0–20% of other sterols and stanols. This starting material containing β-sitosterol, or β-sitosterol may be mixed with the food grade oil in an amount of 0.5–80%, preferably 10–30%, the resulting pasty product having an appearance and a viscosity closely resembling those of butter, and being easy to handle. The higher the percentage of β-sitosterol in the mixture, the harder the mass will be. On the other hand, if the amount of β-sitosterol present in the mixture is less than 10% calculated from the amount of the oil, the viscosity of the mass will decrease, and the consistency thereof is clearly more like that of an oil. As a food grade oil, any cooking oil or any food grade oil or fat, or oil or an oily compound of animal origin, and suitable for human consumption may be used, for instance cod-liver oil, or any edible oily substance of plant or animal origin, or mixtures thereof. Preferred oils are rapeseed oil, turnip seed oil, sunflower oil, soy bean oil, corn oil, and olive oil. The amount of oil is 5–90%, preferably 60–85%, by weight of the mass of the mixture. Water used may be any food grade water, the percentage thereof being 5–30%, preferably 10–20%, by weight of the mass of the mixture.

In this method, a mixture of the starting material containing β-sitosterol and oil is heated at the temperature of 80–140° C., preferably at 100–120° C., until the solid starting material containing β-sitosterol is dissolved in oil. After cooling the mixture in a known manner to the temperature of 40–80° C., preferably to 50–70° C., water is added thereto essentially at the temperature of the mixture. Texture stabilizing surface active agents, such as polysorbate (Tween 80, Polysorbat 80), egg lecithin, or soy bean lecithin, known as emulsifying agents, may optionally be added to the mixture in an amount of 0.05–8.0%, by weight. If necessary, stabilizing agents, antioxidants, or other suitable food additives well known in the art, such as sodium chloride, mineral salt, preserving and flavouring agents, and/or various vitamins, for instance the vitamins A and E, food colours and phytophenols may be added. The mixture thus prepared is homogeneous and stable under conventional conditions for storing food products. In the mixture, β-sitosterol is in a partly dissolved and/or microcrystalline form. If required, β-sitosterol may also be dissolved in an oil as described above, and this β-sitosterol/oil mixture may be used as such in food production.

The method of the invention makes it possible to produce, in a simple and economic way, a fat mixture of β-sitosterol which is health beneficial, homogeneous and stable, reduces absorption of cholesterol in the intestine, thus lowering the serum total cholesterol and LDL-cholesterol levels, and contains the β-sitosterol in a partly dissolved and/or microcrystalline form. This method uses a naturally occurring β-sitosterol, and a food grade oil or fat, without any organic solvents or complicated process steps. Even high doses of the resulting homogeneous stable fat mixture containing a naturally occurring β-sitosterol may be consumed safely in food products daily, and used in food production and cooking to replace fat partly or totally. β-sitosterol cannot be detected from food products by senses. By means of the thus prepared food products, absorption of cholesterol in the intestine may be inhibited, and total serum cholesterol and LDL-cholesterol levels may be lowered significantly. In addition, since β-sitosterol replacing fat is not substantially absorbed, the proportion of absorbed fat is reduced, and thus the energy intake lowered.

Fat mixture containing β-sitosterol may be added into food products that comprise fats of animal or plant origin, or mixtures thereof. Suitable food products are various processed meat products such as sausages and cold cuts, processed fish products, food products containing natural fatty acids, dairy products such as cheese, and several other food products containing edible fats or mixtures thereof, for instance sauces and dressings, mayonnaise, spices and spice mixtures, cereal, noodle and pasta products, ice cream, candies, chocolate, cakes, pastries, and the like, as well as edible fats for cooking and baking, and mixtures thereof.

The invention will now be illustrated with some preferred embodiments thereof described in the following examples, however, without intending to limit the invention solely thereto.

EXAMPLES

Method for Producing a Mixture of β-sitosterol and Fat, i.e. a So-called Basic Mixture In the examples, the starting material was a mixture containing β-sitosterol and β-sitostanol in a total amount of 89.2%, α-sitosterol in an amount of 0.1%, campesterol and campestanol in a total amount of 8.9%, and arthenols in a total amount of 0.9%. The starting material had a solid matter content of 98.8%, melting range of 137–138° C., and density of 0.49 kg/dm$^3$.

For convenience, this starting material is referred to in the following as the starting material containing β-sitosterol according to the main component thereof.

Example 1

Basic Mixture Containing β-sitosterol

A mixture was prepared containing 20% by weight of β-sitosterol and 80% by weight of rapeseed oil. The mixture was heated while stirring in a glass jar until the starting material containing β-sitosterol was dissolved in oil. At that point, the temperature was about 110° C., and the test was carried out at normal atmospheric pressure.

After cooling the mixture to about 60° C., tap water having the same temperature as the mixture (60° C.) was added thereto in an amount of about 15%, by weight of the amount of the mixture, triturating in a mortar.

The mixture was initially transparent and oily yellow when examined visually. Suddenly, the addition of water being almost complete, the mixture became opaque and off-white. The mixture was allowed to cool to room temperature (22° C.) while mixing. The final composition of the mixture is shown in Table 1.

TABLE 1

Composition of the basic mixture containing β-sitosterol

| Ingredient | Amount (%, by weight) |
| --- | --- |
| Starting material containing β-sitosterol | 17 |
| Rapeseed oil | 68 |
| Water | 15 |
| Total | 100 |

Based on sensory examination, the mixture of Table 1 was a white fat mass, having a consistency closely resembling that of butter, and containing β-sitosterol in a partly dissolved and/or microcrystalline form. The mixture was practically tasteless.

When stored in a refrigerator, the basic mixture of Table 1 has remained unchanged, based on sensory examination. Up to now, the mixture has been stored for about 6 months.

Example 2
Variation of Concentrations of the Starting Material Containing β-sitosterol in the Mixture Containing Oil and Water With the method of Example 1, mixtures were prepared wherein the proportion of the starting material containing β-sitosterol was 2.5–60% of rapeseed oil. It was observed that the consistency of the basic mixture was most preferable when the concentration of the starting material containing β-sitosterol was between 10% and 20%. The mixture has then an appearance and a viscosity comparable to those of butter, and it is easy to handle.

The higher the proportion of the starting material containing β-sitosterol in the mixture, the harder the consistency thereof will be. Despite the hardness of the mixture, even high proportions of the starting material containing β-sitosterol may be used, as described in Example 11 (Addition of the starting material containing β-sitosterol to a pasta product).

Example 3
Preparation of the Mixture Using Various Food Oils

With the method of Example 1 mixtures were prepared replacing rapeseed oil with sunflower oil, corn oil and olive oil. Mixtures were prepared with each of these oils using three different percentages of β-sitosterol: 5%, 10% and 20%.

Based on a sensory and microscopic examination, the mixtures were similar to those prepared with rapeseed oil, except that the mixture containing olive oil had a greenish colour. This suggests that all food grade oils are very suitable for use in the method of the invention.

Example 4
Addition of a Surface Active Agent to the Basic Mixture of Example 1

It is generally known that surface active agents are necessary for the preparation and stabilization of disperse systems, particularly emulsions. It is often important to use surface active agents able to stabilize the consistency of dispersions, especially for long term storage, for instance to prevent any separation of the emulsion components, or crystallization thereof.

Essentially, the mixtures of example 1 were prepared, containing 2% by weight, calculated from the proportion of the water phase, of emulsifiers generally known as surface active agents such as polysorbate (Tween 80, Polysorbat 80), egg lecithin or soy bean lecithin. The resulting compositions were essentially as shown in Table 1, but each containing about 0.3%, by weight, of a surface active agent.

Addition of a Fat Mixture Containing β-sitosterol to a Food Product

Example 5
Addition of the Mixture Described in Example 1 to Traditional Commercially Available Butter 50% by weight of the basic mixture according to example 1 and 50% by weight of butter (Meijerivoi of Valio, low salt content) were mixed in an ordinary steel mortar at room temperature (about 22° C.). The mixing could be readily carried out without any difficulties.

Based on a sensory evaluation, the result was a uniform, light yellow mass of the colour of butter that felt like ordinary butter in every respect. The taste of the mixture was good and could not be distinguished from that of real butter, except perhaps for a lower salt content.

Example 6
Addition of the Mixture Described in Example 1 to Conventional Commercially Available Rapeseed Margarine 50% by weight of the basic mixture according to example 1 and 50% by weight of rapeseed margarine (Kultarypsi margariini 60, Van der Bergh, Sweden) were mixed in an ordinary steel mortar at room temperature (about 22° C.). The mixture was slightly softer, but having a consistency otherwise similar to that in Example 3 above. The mixing could be readily carried out without any difficulties.

Based on a sensory evaluation, the result was a uniform, light yellow mass of the colour of the original rapeseed margarine that felt like ordinary rapeseed margarine in every respect. The taste of the resulting mixture was good and could not be distinguished from that of the initial margarine, except perhaps for a lower salt content.

Example 7
Addition of the Mixture Described in Example 1 to Ordinary Commercially Available Light Spread 50% by weight of the basic mixture according to example 1 and 50% by weight of light spread (Kevyt Voilevi 40% of Valio having a low salt content) were mixed in an ordinary steel mortar. The mixing could be carried out easily without any problems.

Based on a sensory evaluation, the result was a uniform mass having a light yellow colour, and a feeling throughout similar to those of the initial light spread used. The taste of the resulting mixture was good, and practically, could not be distinguished from that of the initial light spread, except perhaps for a lower salt content.

Example 8
Addition of Salt (Sodium Chloride) to Mixtures Prepared as Described in Examples 1 and 2

Mixtures were prepared as described in examples 1 and 2, adding thereto 0.9% of sodium chloride of the final weight of the mass, using a generally known method. Based on a sensory evaluation, the addition of salt did not impair in any way the properties of these basic mixtures.

Example 9
Evaluation of the Frying Properties of the Masses Described Above

The behaviour of the mixtures containing butter or vegetable margarine described in examples 5 and 6 was studied under simulated frying conditions by frying them in beakers. For comparison, frying of pure butter and margarine was also studied. The mixture containing light spread was not fried because the light spread used as a starting material is not intended for frying.

9.1 Butter as Such

Initially, when pure butter was heated, it formed a bright yellow oil with little bubbles. When the heating was continued, brown precipitated layers appeared. This is how butter normally turns brown.

9.2 Mixture Containing Butter and β-sitosterol

When frying the mixture of example 5, it melted slightly slower and sizzled more than butter heated similarly. Like butter, it formed a bright yellow oil. When the heating was continued, brown spots appeared having the same colour as the spots in butter, but of smaller size. This suggests that said mixture of example 5 is as suitable for frying as commercially available butters.

9.3 Margarine as Such

Also pure margarine formed a bright yellow oil when melted. It sizzled more than butter when heated. On heating, brown spots appear on it, as in the mixture of example 5 containing butter and the basic mixture of example 1.

9.4 Mixture Containing Margarine and β-sitosterol

When frying the mixture of example 6, it was observed that it behaved in the frying test in the same way as pure margarine and substantially in the same way as the mixture of example 5. This suggests that the mixture is as suitable for heating as commercially available margarines.

9.5 Conclusions of the Tests in Example 9

In this frying test, differences in fat browning seemed to be due to the type of fat used (butter or rapeseed margarine), not to the presence of the basic mixture containing β-sitosterol.

Example 10

Addition of the Mixture Described in Example 1 to Dairy Products

50% by weight of the basic mixture according to example 1 and 50% by weight of mayonnaise (Heinz Mayonnaise, H. J. Heinz B. V., Holland) were mixed in an ordinary steel mortar at room temperature (about 22° C.). The mixture was mixed in the same manner with a sour cream product (Smetana from Valio) and with a cream cheese product (Hovi cream cheese from Valio). Mixing with these food products could be carried out easily without any difficulties.

Example 11

Addition of the Starting Material Containing β-sitosterol to a Pasta Product

β-sitosterol was heated with the amount of oil needed for pasta preparation until either β-sitosterol dissolved in oil, or an opalescent uniform flowing liquid was formed, depending on the ratio of β-sitosterol to oil. This liquid was allowed to cool while triturating it. To the resulting cooled mixture was added either water, or an egg mixture and water, or an egg mixture while triturating at the same time to form an emulsion. A suitable amount of durum wheat flour and salt were then added by kneading the dough. Water was added as required during kneading. The result was uniform pasta wherein β-sitosterol could not be detected visually, nor tasted. The amount of β-sitosterol in the pasta was as much as 2 g/100 g of fresh pasta. Amounts exceeding this are not necessary in view of the weight of a pasta portion (125 g of fresh pasta/portion) and considering the suitable concentration of β-sitosterol for the activity thereof. Table 2 shows examples of pasta dough compositions.

Pasta sheets were prepared in a usual way from this pasta dough. The pasta may be served either as fresh pasta or it may be dried for a longer term storage. Both fresh and dried pasta products were cooked in ample water for as long as 10 minutes. β-sitosterol was not released from the pasta either into the cooking water or into the rinsing water of the cooked pasta.

The properties of the pasta completely corresponded to those of ordinary pasta prepared without β-sitosterol.

TABLE 2

Examples of the compositions of pasta doughs

| Ingredient | Pasta without egg amount (g) / 100 grams of pasta dough | Pasta with egg amount (g) / 100 grams of pasta dough |
| --- | --- | --- |
| β-sitosterol | 1.7 | 1.7 |
| Rapeseed oil | 1.3 | 1.3 |
| Durum wheat flour | 62.6 | 61.8 |
| Egg | — | 29.0 |
| Water | about 34 [1] | about 5 [1] |
| Salt | 0.8 | 0.8 |

[1] Suitable water amount may vary depending for instance on the type of durum wheat flour.

Example 12

Addition of the Basic Mixture Containing β-sitosterol to Pizza

TABLE 3

Pizza recipe

| | Ingredient | Pizza | Pizza with basic mixture containing β-sitosterol |
| --- | --- | --- | --- |
| Dough | water | 200.0 g | 200 g |
| | yeast | 25.0 g | 25.0 g |
| | salt | 3.0 g | 3.0 g |
| | wheat flour | 298.8 g | 298.8 g |
| Garnish | ground meat (pork + beef) | 250.0 g | 250.0 g |
| | onion | 130.0 g | 130.0 g |
| | crushed tomatoes | 400.0 g | 400.0 g |
| | oregano | 1.2 g | 1.2 g |
| | basil | 1.0 g | 1.0 g |
| | crushed garlic | 3.0 g | 3.0 g |
| | salt | 6.0 g | 6.0 g |
| | black pepper powder | 0.5 g | 0.5 g |
| | paprika powder | 0.5 g | 0.5 g |
| | basic mixture containing β-sitosterol* | 0.00 g | 59.0 g |
| Topping | grated cheese | 150.0 g | 150.0 g |
| | total | 1471.0 g | 1530.0 g |

*The composition of the basic mixture used is shown in Table 1.

The pizzas were baked at 225° C. for about 25–30 minutes.

The properties of the pizza containing β-sitosterol completely corresponded to those of the pizza prepared without β-sitosterol.

Example 13

Addition of the Basic Blend Containing β-sitosterol to Meatballs

TABLE 4

Meatball recipe

| Ingredient | % | g |
|---|---|---|
| Prefabricated meatball mix** | 10.5 | 52.5 |
| Water | 36.5 | 182.5 |
| Ground meat (pork + beef) | 53 | 265.0 |
|  | 100 | 500.0 |

TABLE 5

Meatball recipe added with the basic blend containing β-sitosterol

| Ingredient | % | g |
|---|---|---|
| Prefabricated meatball mix** | 10.1 | 52.5 |
| Water | 35 | 182.5 |
| Ground meat (pork + beef) | 50.8 |  |
| Basic blend containing β-sitosterol* | 4.1 | 21.25 |
|  | 100 | 521.25 |

*Table 3 shows the composition of the basic blend used.
**Meatball Mix is an industrially produced mixture of dry ingredients for meatballs of Northern type containing seasonings, starch, soyaflour and bread crumbs.

Meatballs were baked at 225° C. for 20 mins.

The meat mixture did not stick to hands, and the properties of the meatballs containing β-sitosterol were comparable to those of ordinary meatballs without any β-sitosterol.

Example 14

Addition of the Basic Mixture Containing β-sitosterol to Bread Rolls

TABLE 6

Recipe for bread rolls

| Ingredient | % | g |
|---|---|---|
| Water | 44 | 461.0 |
| Yeast | 4.5 | 47.5 |
| Salt | 1.1 | 11.7 |
| Syrup | 0.3 | 3.6 |
| Bread flour mixture | 46.3 | 525.3 |
| Oat flakes | 3.8 | 40.0 |
|  | 100 | 1089.1 |

TABLE 7

Recipe for bread rolls with a basic mixture containing β-sitosterol added thereto

| Ingredient | % | g |
|---|---|---|
| Water | 3.7 | 461.0 |
| Yeast | 3.8 | 47.5 |
| Salt | 0.9 | 11.7 |
| Syrup | 0.2 | 3.6 |
| Bread flour mixture | 42.2 | 525.3 |
| Oat flakes | 3.2 | 40.0 |

TABLE 7-continued

Recipe for bread rolls with a basic mixture containing β-sitosterol added thereto

| Ingredient | % | g |
|---|---|---|
| Basic mixture containing β-sitosterol* | 12.7 | 158.0 |
|  | 100 | 1247.1 |

*Composition of the basic mixture containing β-sitosterol is shown in Table 1.

The basic mixture containing β-sitosterol could be mixed into the dough very well and the dough was easy to handle and knead since it was not sticky. The properties of the bread rolls containing β-sitosterol totally corresponded to those of the rolls prepared without β-sitosterol.

Example 15

Addition of the Basic Mixture Containing β-sitosterol to a Sauce Made with Milk

TABLE 8

Recipe for a sauce with milk

| Ingredient | % | g |
|---|---|---|
| Milk | 93.7 | 390.0 |
| Salt | 1 | 4 |
| Bread flour mixture | 5.4 | 22.3 |
|  | 100 | 416.3 |

TABLE 9

Recipe for a sauce with milk and with a basic mixture containing β-sitosterol added thereto

| Ingredient | % | g |
|---|---|---|
| Milk | 85.9 | 390 |
| Salt | 0.9 | 4 |
| Bread flour mixture | 4.9 | 22.3 |
| Basic mixture containing β-sitosterol* | 8.3 | 37.5 |
|  | 100 | 453.8 |

*Composition of the basic mixture containing β-sitosterol is shown in Table 1.

Fat was melted in a saucepan, and then flour was added thereto. The mixture was allowed to boil, and cold milk was added in two portions. The fat was well and evenly mixed in the sauce. The properties of a milky sauce wherein fat was replaced with the basic mixture containing β-sitosterol completely corresponded to those of the sauce prepared using ordinary fat.

REFERENCES

1) Jousilahti P, Vartiainen E, Tuomilehto J, Puska P: The Lancet 348/9027), pp. 567–572. 1996
2) Claus E P, Tyler V E & Brady L R: *Pharmacognosy* 6th edition, Lea & Febiger, London, 1970, pp. 165–157
3) Jones P J H et al.: Canadian Journal of Physiology & Pharmacology 75(3): 217–227, 1997
4) Pollak O J, Kritchecsky D: Monogr Atheroscler. 10: 1–219, 1981
5) Vahoyny G V, Kritchavsky D.: Plant and marine sterols and cholesterol metabolism. In Spiller GA., ed. Nutritional Pharmacology. New York, N.Y.: Alan R Liss Inc; 1981 pp. 31–72

6) Vahoyny G V, Kritchevsky D.: Plant and marine sterols and cholesterol metabolism. In Spiller GA, ed. Nutritional Pharmacology. New York N.Y.: Alan R Liss Inc; 1981 pp. 31–72

7) Tilvis R S, Miettinen T A: Am J Clin Nutr.: 43; 92–97, 1986

8) Mattson F H; Grundy S M, Crouse J R: Am J Clin Nutr. 35, 697–700, 1982

9) Steinegger E & Hänsel R: Pharmakognosie, 5. Aufl., Springer-Lehrbuch, Berlin-Haidelberg-New York, 1992, p. 195

10) Hänsel R & Haas H.: Therapie mit Phutopharmaka, Springer-Verlag, Berlin-Heidelberg-New York-Tokyo, 1983 pp. 187–188

11) Hänsel R: Phutopharmaka, Grundlagen und Praxis, 2. Auflage, Springer-Verlag, Berlin-Heidelberg-New York, 1991 pp. 192–193

12) Jones P J H et al.: Canadian Journal of Physiology & Pharmacology 75(3): 217–227, 1997

13) Field, F J et al.: Journal of Lipid Research. 38(2): 348–360, 1997

14) Richter W et al.: Current Research. 57(7): 497–505, 1996

15) Mattson F H et al.: American Journal of Clinical Nutrition. 35(4): 697–700, 1982

16) Uchita E et al.: Japanese Journal of Pharmacology. 33(1): 103–12, 1983

17) Vahouny G B et al.: American Journal of Clinical Nutrition. 37(5): 805–9, 1983

What is claimed is:

1. A method for producing a fatty blend of β-sitosterol, or of β-sitosterol and β-sitostanol, which is useful for lowering the serum total cholesterol and LDL-cholesterol levels, which method consists of:

forming a mixture by dissolving 0.5–80 wt % of a starting material containing β-sitosterol, or β-sitosterol and β-sitostanol, in 5–90 wt % of oil or fat, or mixtures thereof, by heating at a temperature of 80–140° C. until the starting material containing β-sitosterol or β-sitostemol and β-sitostanol is dissolved;

cooling the mixture to a temperature of 40–80° C.;

during the cooling adding 5–30 wt % of water with a temperature essentially similar to that of the mixture to the mixture, and agitating the mixture and the water to form a homogeneous and stable dispersion of the mixture in the water, wherein the starting material containing β-sitosterol or β-sitosterol and β-sitostanol is in a partly dissolved and/or microcrystalline form.

2. The method according to claim 1, wherein the oil or fat is a food grade oily substance of plant or animal origin, or a mixture thereof.

3. The method according to claim 1, wherein the oil contains sunflower oil, rapeseed oil, turnipseed oil, soyabean oil, olive oil, or corn oil.

4. The method according to claim 1, wherein a food additive, sodium chloride, mineral salt, preserving or flavouring agents or vitamins, or mixtures thereof is/are added to the mixture.

5. A fat composition containing β-sitosterol, or β-sitosterol and β-sitostanol, that lowers the serum total cholesterol and LDL-cholesterol levels, which composition consists of:

(a) 0.5–80 wt % of a starting material containing β-sitosterol, or β-sitosterol and β-sitostanol dissolved in oil or fat or mixtures thereof, and (b) 5–30 wt % of water, wherein the β-sitosterol, or β-sitosterol and β-sitostanol, and oil or fat or mixtures thereof, are dispersed in the water, and the starting material containing β-sitosterol, or β-sitosterol and β-sitostanol, is in a partly dissolved and/or microcrystalline form, and the composition is stable and homogeneous at room and refrigerator temperature, based on physical and sensory evaluations.

6. The composition according to claim 5, wherein the oil or fat is a food grade oily substance of plant or animal origin, or a mixture thereof.

7. The composition according to claim 5, wherein the oil contains sunflower oil, rapeseed oil, turnipseed oil, soybean oil, olive oil, or corn oil.

8. The composition according to claim 5, wherein the composition further contains a food additive, sodium chloride, mineral salt, preserving or flavouring agents or various vitamins, or mixtures thereof.

9. A food product comprising the composition according to claim 5.

10. A food product according to claim 9, wherein the food product is selected from the group consisting of fats of animal or plant origin or mixtures thereof, food products containing natural fatty acids, dairy products, and food products containing edible fats or mixtures thereof.

11. A method for adding β-sitosterol, or β-sitosterol and β-sitostanol, for the purpose of lowering serum total cholesterol and LDL-cholesterol levels, into food products, which method comprises:

forming an aqueous dispersion by a method which consists of (a) forming a mixture by dissolving 0.5–80 wt % of a starting material containing β-sitosterol, or β-sitosterol and β-sitostanol, in 5–90 wt % of oil, fat or mixtures thereof by heating at a temperature of 80–140° C. until the starting material containing β-sitosterol or β-sitosterol and β-sitostanol is dissolved;

cooling the mixture to a temperature of 40–80° C.;

during the cooling adding 5–30 wt % of water, with a temperature essentially similar to that of the mixture, to the mixture;

agitating the mixture and the water to form a homogeneous and stable dispersion of the mixture in the water, wherein the starting material containing β-sitosterol, or β-sitosterol and β-sitostanol, is in a partly dissolved and/or microcrystalline form; and (b) mixing the resulting dispersion into food ingredients during a food production process.

12. The method according to claim 4, wherein the vitamins comprise vitamins A and E.

13. The composition according to claim 8, wherein the vitamins comprise vitamins A and E.

14. A method of lowering serum total cholesterol and LDL-cholesterol levels in a person in need thereof, which comprises the oral administration of the composition according to claim 6.

15. A food product according to claim 10, wherein the food product is selected from the group consisting of sauces, dressings, mayonnaise, spices, cereal products, ice cream, candies, chocolate, cakes and pastries.

16. A method of lowering serum total cholesterol and LDL-cholesterol in a person in need thereof, which comprises the oral administration of a food product obtained by the method according to claim 11.

* * * * *

UNITED STATES PATENT AND TRADEMARK OFFICE
CERTIFICATE OF CORRECTION

PATENT NO.   : 6,531,463 B1
DATED        : March 11, 2003
INVENTOR(S)  : Jouko Yliruusi et al.

It is certified that error appears in the above-identified patent and that said Letters Patent is hereby corrected as shown below:

Column 11,
Line 42, "β-sitostemol" should read -- β-sitosterol --.

Column 12,
Line 55, "levels in" should read -- slevel, in --.
Line 63, "LDL-cholesterol in" should read -- LDL cholesterol, in --

Signed and Sealed this

Twenty-first Day of September, 2004

JON W. DUDAS
*Director of the United States Patent and Trademark Office*